US00PP15987P2

(12) United States Plant Patent
Hoogendoorn

(10) Patent No.: US PP15,987 P2
(45) Date of Patent: Sep. 20, 2005

(54) ***ALSTROEMERIA* PLANT NAMED 'ZAPRINOUS'**

(50) Latin Name: *Alstroemeria hybrida*
Varietal Denomination: Zaprinous

(75) Inventor: Cornelius Arie Hoogendoorn, Aarlanderveen (NL)

(73) Assignee: Van Zanten Plants, B.V., Rijsenhout (NL)

( * ) Notice: Subject to any disclaimer, the term of this patent is extended or adjusted under 35 U.S.C. 154(b) by 26 days.

(21) Appl. No.: 10/945,172

(22) Filed: Sep. 20, 2004

(51) Int. Cl.[7] ..... A01H 5/00
(52) U.S. Cl. ..... Plt./309
(58) Field of Search ..... Plt./309

*Primary Examiner*—Kent Bell
(74) *Attorney, Agent, or Firm*—C. A. Whealy

(57) ABSTRACT

A new and distinct cultivar of *Alstroemeria* plant named 'Zaprinous', characterized by its compact and mounded plant habit; vigorous growth habit; purple-colored flowers; and good postproduction longevity.

1 Drawing Sheet

Botanical classification/cultivar designation: *Alstroemeria hybrida* cultivar Zaprinous.

BACKGROUND OF THE INVENTION

The present Invention relates to a new and distinct cultivar of *Alstroemeria* plant, botanically known as *Alstroemeria hybrida*, commercially used as a container *Alstroemeria*, and hereinafter referred to by the name 'Zaprinous'.

The new *Alstroemeria* is a product of a planned breeding program conducted by the Inventor in Rijsenhout, The Netherlands. The objective of the breeding program was to develop new compact container *Alstroemeria* cultivars with desirable flower and plant qualities, attractive flower colors and excellent postproduction longevity.

The new *Alstroemeria* originated from a cross-pollination made by the Inventor in 1999 in Rijsenhout, The Netherlands, of a proprietary *Alstroemeria hybrida* selection identified as 97120-003PN, not patented, as the female, or seed, parent with a proprietary *Alstroemeria hybrida* selection identified as 95197-002D, not patented, as the male, or pollen, parent. The new *Alstroemeria* was discovered and selected by the Inventor as a flowering plant within the progeny of the stated cross-pollination in a controlled environment in Rijsenhout, The Netherlands in 1999.

Asexual reproduction of the new cultivar by root divisions in a controlled environment in Rijsenhout, The Netherlands, since June, 1999, has shown that the unique features of this new *Alstroemeria* are stable and reproduced true to type in successive generations of asexual propagation.

SUMMARY OF THE INVENTION

Plants of the cultivar Zaprinous have not been observed under all possible environmental conditions. The phenotype may vary somewhat with variations in environment such as temperature and light intensity without, however, any variance in genotype.

The following traits have been repeatedly observed and are determined to be the unique characteristics of 'Zaprinous'. These characteristics in combination distinguish 'Zaprinous' as a new and distinct cultivar:

1. Compact and mounded plant habit.
2. Vigorous growth habit.

3. Purple-colored flowers.
4. Good postproduction longevity.

Plants of the new *Alstroemeria* can be compared to plants of the female parent selection. In side-by-side comparisons conducted in Rijsenhout, The Netherlands, plants of the new *Alstroemeria* differed primarily from plants of the female parent selection in flower coloration as plants of the female parent selection had pink-colored flowers.

Plants of the new *Alstroemeria* can be compared to plants of the male parent selection. In side-by-side comparisons conducted in Rijsenhout, The Netherlands, plants of the new *Alstroemeria* differed primarily from plants of the male parent selection in flower coloration as plants of the female parent selection had red-colored flowers.

Plants of the new *Alstroemeria* can also be compared to plants of the cultivar Staprilene, disclosed in U.S. Plant Pat. No. 11,683. In side-by-side comparisons conducted in Rijsenhout, The Netherlands, plants of the new *Alstroemeria* differed from plants of the cultivar Staprilene in the following characteristics:

1. Plants of the new *Alstroemeria* were smaller than plants of the cultivar Staprilene.
2. Plants of the new *Alstroemeria* had smaller leaves than plants of the cultivar Staprilene.
3. Plants of the new *Alstroemeria* had smaller flowers than plants of the cultivar Staprilene.
4. Plants of the new *Alstroemeria* and the cultivar Staprilene differed in flower coloration.
5. Flowers of plants of the new *Alstroemeria* had fewer stripes than flowers of plants of the cultivar Staprilene.

BRIEF DESCRIPTION OF THE PHOTOGRAPH

The accompanying colored photograph illustrates the overall appearance of the new *Alstroemeria*, showing the colors as true as it is reasonably possible to obtain in colored reproductions of this type. Colors in the photograph may differ slightly from the color values cited in the detailed botanical description which accurately describe the colors of the new *Alstroemeria*. The photograph comprises a side perspective view of a typical flowering plant of 'Zaprinous' grown in a container.

DETAILED BOTANICAL DESCRIPTION

The aforementioned photograph and following observations and measurements describe plants of the new *Alstroemeria* grown in 17-cm containers in Rijsenhout, The Netherlands in a glass-covered greenhouse in ground beds. During the production of the plants, day temperatures ranged from 15 to 25° C., night temperatures ranged from 10 to 15° C. and light levels averaged 5,000 lux. Plants used for the photograph and description were about six months-old. The photograph and the description were taken during February. Color references are made to The Royal Horticultural Society Colour Chart, 1995 Edition, except where general terms of ordinary dictionary significance are used.

Botanical classification: *Alstroemeria hybrida* cultivar Zaprinous.

Parentage:

*Female parent.*—Proprietary *Alstroemeria hybrida* selection identified as 97120-003PN, not patented.

*Male parent.*—Proprietary selection of *Alstroemeria hybrida* identified as 95197-002D, not patented.

Propagation:

*Type.*—By root divisions.

*Root description.*—Fibrous, fleshy, thick; white, close to 155D, in color.

*Rooting habit.*—Freely branching.

*Rhizomes.*—Shape: Elongate; rounded. Length: About 10 to 30 cm. Diameter: About 3 to 10 mm. Texture: Smooth. Color: Close to 155D.

Plant description:

*Plant habit.*—Compact and mounded growth habit; freely branching, bushy appearance. Vigorous growth habit.

*Plant height.*—About 15 to 25 cm.

*Plant diameter* (*spread*).—About 30 to 40 cm.

*Lateral stem description.*—Aspect: Mostly upright. Quantity per plant: About 10 to 15. Length: About 15 to 20 cm. Diameter: About 3 to 5 mm. Internode length: About 0.5 to 1.5 cm. Strength: Strong. Texture: Glabrous. Color: Close to 145A; glossy.

*Foliage description.*—Leaves asymmetrical; sessile. Length: About 6 to 9 cm. Width: About 1.7 to 2.5 cm. Shape: Lanceolate. Apex: Acute. Base: Attenuate. Margin: Entire. Texture, upper and lower surfaces: Smooth, glabrous. Venation pattern: Parallel. Color: Developing and fully developed foliage, upper surface: Close to 135A; slightly glossy. Developing and fully developed foliage, lower surface: Close to 137A. Venation: Upper surface, close to 135A; lower surface, close to 137A.

Flower description:

*Flower type and habit.*—Single cup-shaped flowers arranged in compound umbels. Perianth segments separate. Freely and continuously flowering. Flowers not persistent.

*Natural flowering seasons.*—Flowering continuous during the spring in The Netherlands.

*Fragrance.*—None detected.

*Flower longevity on the plant.*—About four weeks.

*Flower longevity as a cut flower.*—About 18 to 20 days.

*Flower buds.*—Length: About 3 to 3.5 cm. Diameter: About 1.3 to 1.7 cm. Shape: Roughly ovoid. Color: Close to 145A.

*Umbel height.*—About 8 to 10 cm.

*Umbel diameter.*—About 12 to 14 cm.

*Number of flowers per umbel.*—About four to ten.

*Flower length* (*height*).—About 6 to 7 cm.

*Flower diameter.*—About 5.5 to 6.5 cm.

*Flower depth.*—About 5 to 6 cm.

*Perianth.*—Arrangement: Six arranged in two whorls, each whorl with two lateral and one median segments. Size, inner perianth: Length, lateral segments: About 5.5 to 6 cm. Length, median segment: About 5 to 5.5 cm. Width, lateral segments: About 1.8 to 2 cm. Width, median segment: About 1.8 to 2 cm. Size, outer perianth: Length, lateral segments: About 5 to 5.5 cm. Length, median segment: About 5.5 to 6.5 cm. Width, lateral segments: About 2.7 to 3.5 cm. Width, median segment: About 3 to 3.3 cm. Shape, inner perianth, lateral and median segments: Oblanceolate. Shape, outer perianth, lateral and median segments: Obovate. Apex, inner perianth, lateral and median segments: Wishbone-shaped. Apex, outer perianth, lateral and median segments: Bracket-shaped. Base, inner and outer perianths, lateral and median segments: Attenuate. Margin, inner and outer perianths, lateral and median segments: Entire; moderately undulate. Texture, inner and outer perianths, lateral and median segments: Smooth, glabrous; velvety. Color, inner perianth: When opening and fully opened, lateral segments, upper surface: Towards the apex, 72B; towards the base, close to 155B, stripes, purplish close to 187A; tip, greenish white. When opening and fully openined, median segment, upper surface: Towards the apex, 70B; towards the base, 155A; stripes, purplish close to 187A; tip, greenish white. When opening and fully opened, lateral segments, lower surface: Towards the apex, 72B; towards the base, close to 155B; tip, greenish white. When opening and fully opened, median segment, lower surface: Towards the apex, 70B; towards the base, 155A; tip, greenish white. Color, outer perianth: When opening and fully opened, lateral segments, upper surface: Close to 59A; towards the margins, close to 77A; few stripes, purplish close to 187A; tip, greenish white. When opening and fully opened, median segment, upper surface: Close to 59A; towards the margins, close to 77A; tip, greenish white. When opening and fully opened, lateral segments, lower surface: Close to 59A; towards the margins, close to 77A; tip and venation, greenish white. When opening and fully opened, median segment, lower surface: Close to 59A; towards the margins, close to 77A; tip and venation, greenish white. Peduncles: Length: About 1 to 1.5 cm. Diameter: About 2 to 3 mm. Strength: Strong. Angle: About 30 to 45° from vertical. Texture: Smooth, glabrous. Color: Close to 144A.

*Pedicels.*—Length: About 5 to 10 mm. Diameter: About 2 to 4 mm. Strength: Strong. Angle: About 30 to 45° from vertical. Texture: Smooth, glabrous. Color: Close to 144A.

*Reproductive organs.*—Stamens: Quantity per flower: Six. Filament color: Brownish purple. Anther shape: Elliptical. Anther length: About 2 mm. Anther diameter: About 1 mm. Anther color: Close to 166A. Pollen amount: Abundant. Pollen color: Brown. Pistils: Quantity per flower: One. Style length: About 4 to 5 cm. Style color: Purple. Stigma color: Purple. Ovary color: Close to 144B.

*Fruit.*—Shape: Globular. Color: Brownish.

Disease/pest resistance: Plants of the new *Alstroemeria* have not been observed to be resistant to pathogens and pests common to *Alstroemerias.*

Temperature tolerance: Plants of the new *Alstroemeria* have been observed to tolerate temperatures from −5 to 40° C.

It is claimed:

1. A new and distinct cultivar of *Alstroemeria* plant named 'Zaprinous', as illustrated and described.

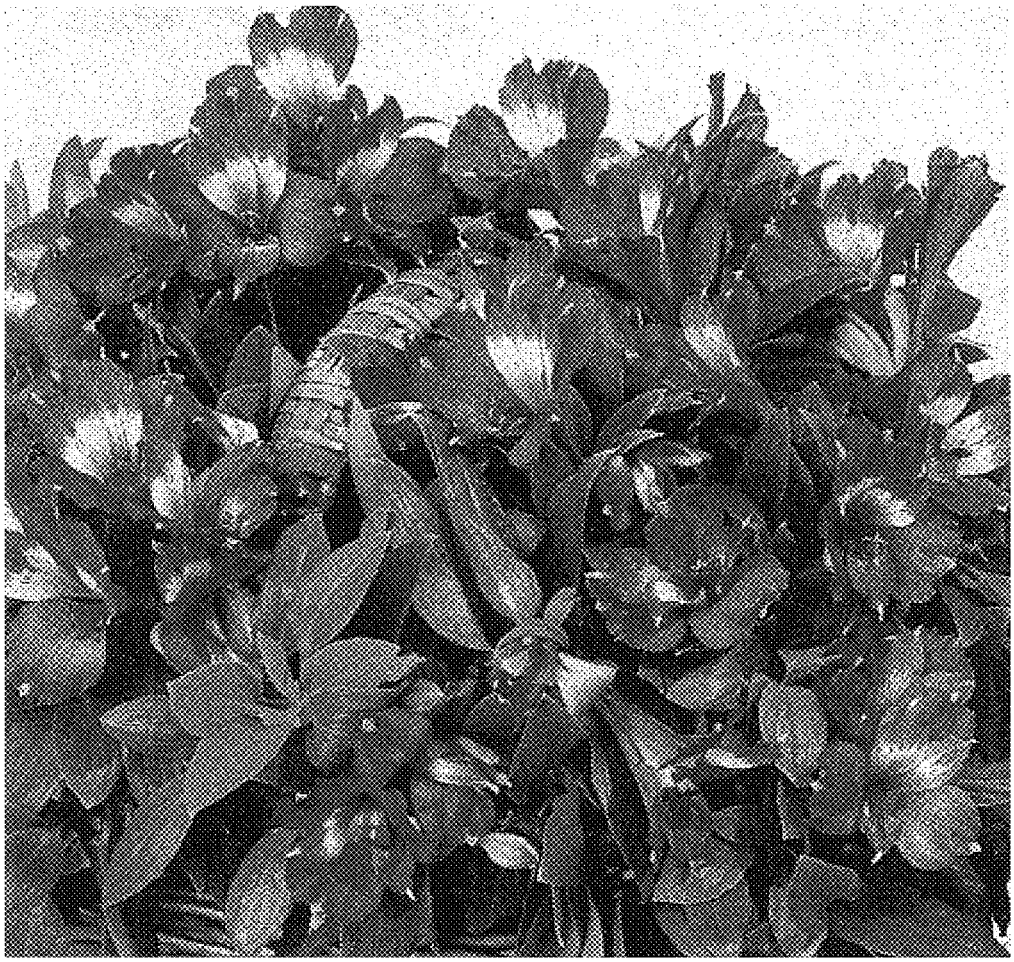

* * * * *